United States Patent
Matsuzawa et al.

(10) Patent No.: US 8,903,038 B2
(45) Date of Patent: Dec. 2, 2014

(54) X-RAY CT DEVICE

(75) Inventors: Yohei Matsuzawa, Nasushiobara (JP);
Tomiya Sasaki, Nasushiobara (JP);
Hiroshi Hori, Nasushiobara (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 462 days.

(21) Appl. No.: 13/405,735

(22) Filed: Feb. 27, 2012

(65) Prior Publication Data

US 2012/0230465 A1    Sep. 13, 2012

(30) Foreign Application Priority Data

Mar. 9, 2011   (JP) ................................. 2011-051700

(51) Int. Cl.
*H05G 1/04*   (2006.01)
*H05G 1/02*   (2006.01)
*A61B 6/03*   (2006.01)
*A61B 6/00*   (2006.01)

(52) U.S. Cl.
CPC . *A61B 6/035* (2013.01); *A61B 6/56* (2013.01);
*A61B 6/588* (2013.01)
USPC .............................. 378/13; 378/197; 378/210

(58) Field of Classification Search
CPC ......... A61N 5/01; A61N 5/1081; B25J 9/026;
H05G 1/00; H05G 1/02; H05G 1/04; H05G 1/06

USPC ......... 378/4–20, 91, 193, 197, 203, 204, 210, 378/901
See application file for complete search history.

(56) References Cited

U.S. PATENT DOCUMENTS

| | | | |
|---|---|---|---|
| 7,991,115 B2 * | 8/2011 | Matsuzawa et al. | 378/63 |
| 8,536,547 B2 * | 9/2013 | Maurer et al. | 250/492.3 |
| 2006/0222143 A1 | 10/2006 | Du | |
| 2011/0101246 A1 * | 5/2011 | Yajima et al. | 250/492.3 |
| 2011/0101254 A1 * | 5/2011 | Yajima et al. | 250/515.1 |
| 2011/0220809 A1 * | 9/2011 | Yajima et al. | 250/396 R |

FOREIGN PATENT DOCUMENTS

| | | |
|---|---|---|
| JP | 02-159260 A | 6/1990 |
| JP | 2006-230783 | 9/2006 |

OTHER PUBLICATIONS

Office Action issued Sep. 30, 2014 in Japanese Patent Application No. 2011-051700 (with English Translation).

* cited by examiner

*Primary Examiner* — Anastasia Midkiff
(74) *Attorney, Agent, or Firm* — Oblon, Spivak, McClelland, Maier & Neustadt, L.L.P.

(57) ABSTRACT

According to one embodiment of the present invention, an X-ray CT device includes: a front dome cover and rear dome cover that include a fixed cover and a plurality of segmented movable covers; a slide mechanism that enables the movable covers to slide relative to the fixed cover; and a dome-diameter driving unit that controls the slide mechanism to change a dome diameter of a gantry dome.

16 Claims, 8 Drawing Sheets

X-RAY CT DEVICE

CROSS-REFERENCE TO RELATED APPLICATION

This application is based upon and claims the benefit of priority from the prior Japanese Patent Application No. 2011-051700 filed on Mar. 9, 2011, the entire contents of which are incorporated herein by reference.

FIELD

Embodiments of the present invention relate to an X-ray CT device.

BACKGROUND

In an X-ray CT (Computed Tomography) device, which is one of medical image diagnosis devices, X rays generated from an X-ray tube passes through a test subject. An image is taken as a pair of X-ray detectors, which is so disposed as to face the X-ray tube, rotates around the test subject. As a result, a tomographic image of the test subject can be obtained. A portion that rotates the X-ray tube and a pair of X-ray detectors is referred to as a rotation unit. A portion that supports the rotation unit is referred to as a fixed unit. Conventionally, an exterior cover of the fixed unit mainly includes a front dome cover and a rear dome cover. An opening (gantry dome) is formed at a portion that a bed between the facing X-ray tube and the X-ray detectors enters. The above is formed by combining integral-molding parts or a plurality of parts.

Moreover, on an internal wall surface of the gantry dome, in order to prevent a test subject from putting a hand or the like into the high-speed rotation unit by accident, a dome cover sheet is provided as an X-ray irradiation window in terms of safety. Before being attached, the dome cover sheet is usually in the form of a sheet. The dome cover sheet is attached to the internal wall surface of the gantry dome, which is made up of the front dome cover and the rear dome cover, so as to be in the form of a cylinder. Depending on the product, the dome cover sheet may be in the form of a cylinder from the beginning. Accordingly, the dome diameter of the gantry dome, which is made by assembling the exterior covers, is fixed, and the configuration does not allow the dome diameter to vary.

If the distance between the X-ray tube and the X-ray detectors is reduced, magnification radiography becomes mechanistically available. The only way to carry out magnification radiography with the current dome-cover structure is to ensure a space inside the rotation unit by designing a small dome diameter from the beginning and shorten the distance (SID: Source Image Distance) between the X-ray tube and the X-ray detectors. However, when the dome diameter is simply made smaller as described above, for example, in the case where a test subject has a large physique or any other case, the problem is that it is not possible to meet the demand of increasing the dome diameter even at the time of normal radiography.

One embodiment of the present invention is to provide an X-ray CT device whose dome diameter is variable.

DETAILED DESCRIPTION

According to embodiments of the present invention, what is provided is an X-ray CT device that includes: a front dome cover and rear dome cover that include a fixed cover and a plurality of segmented movable covers; a slide mechanism that enables the movable covers to slide relative to the fixed cover; and a dome-diameter driving unit that controls the slide mechanism to change a dome diameter of a gantry dome.

Hereinafter, embodiments for carrying out the invention will be described in detail with reference to FIGS. 1 to 9.

First Embodiment

Figure 1:
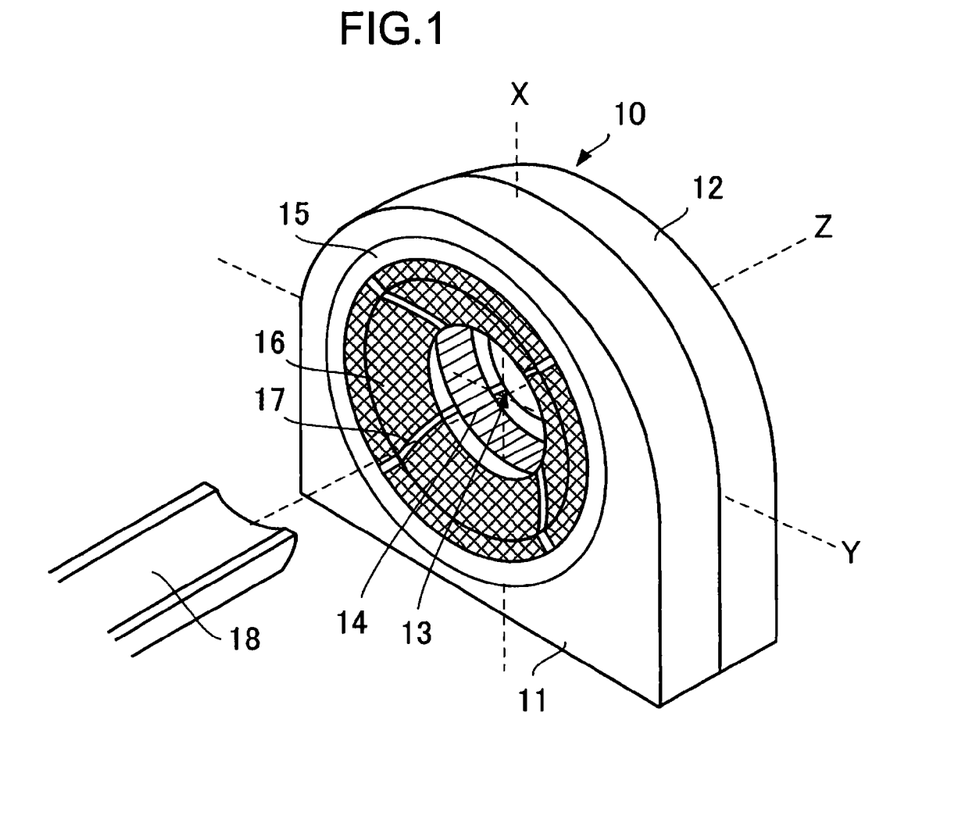
FIG. 1 is a diagram showing the overall configuration of an X-ray CT device according to a first embodiment of the present invention.

A gantry 10 of an X-ray CT device of the present embodiment includes a front dome cover 11 and a rear dome cover 12, which make up a gantry dome 13. On an internal wall surface of the gantry dome 13, a dome cover sheet 14 is provided as an X-ray irradiation window. The front dome cover 11 and the rear dome cover 12 each include a fixed cover 15; a plurality of segmented movable covers 16; and an elastic material 17, which connects adjacent movable covers 16 together. A mechanism is so provided on each movable cover 16 as to allow the movable cover 16 to slide radially, thereby causing the diameter of the gantry dome to expand and contract. As the dome diameter expands and contracts to have a different diameter, a gap between the movable covers 16 emerges. The gap is absorbed by the elastic material 17. The elastic material 17 may be made of a material that has elasticity, or may have a bellows structure. According to the present embodiment, for ease of explanation, since the front dome cover 11 and the rear dome cover 12 are of a symmetrical structure, the front and rear surfaces of the gantry are the same in structure. Moreover, a side cover, a top cover or the like, which may exist depending on the product, is contained in the front dome cover 11 and the rear dome cover 12 and is shown integrally.

A patient (test subject) is allowed to lie on a bed 18 of the X-ray CT device whose dome diameter is variable as described above. Then, the bed 18 moves into the gantry dome 13. A cross-sectional image of an image-taking magnification corresponding to the dome diameter is scanned and obtained.

Figure 2:
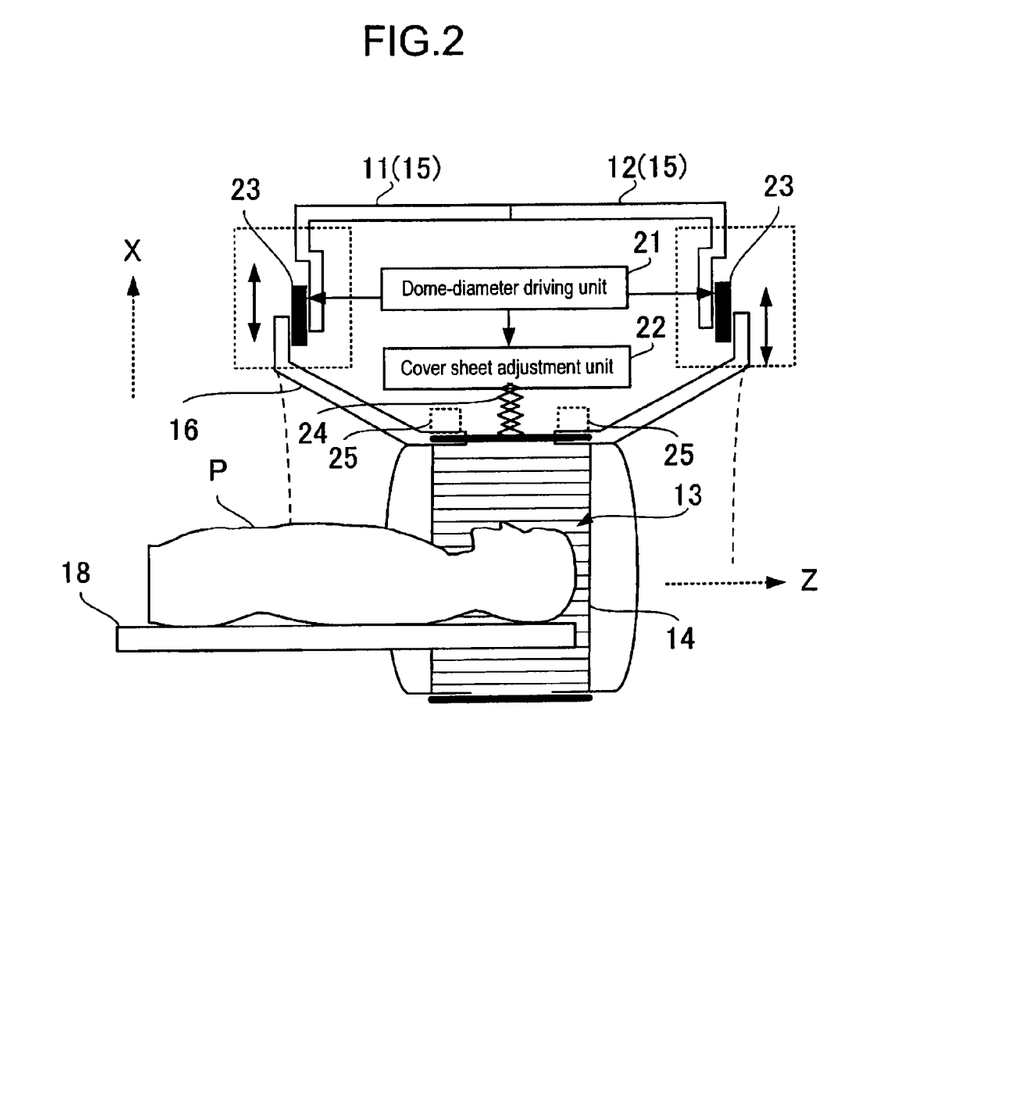
FIG. 2 is a cross-sectional diagram of a dome-diameter variable structure of the X-ray CT device taken along plane X-Z according to the embodiment.
Figure 3:
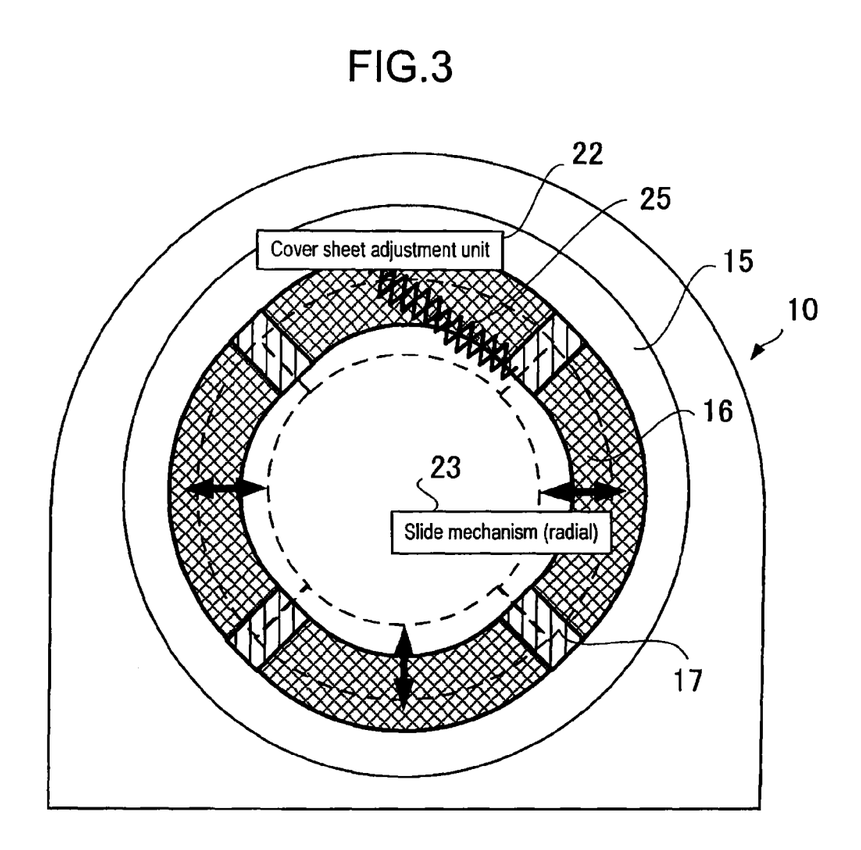
FIG. 3 is a front view of the dome-diameter variable structure of the X-ray CT device according to the embodiment.
Figure 4:
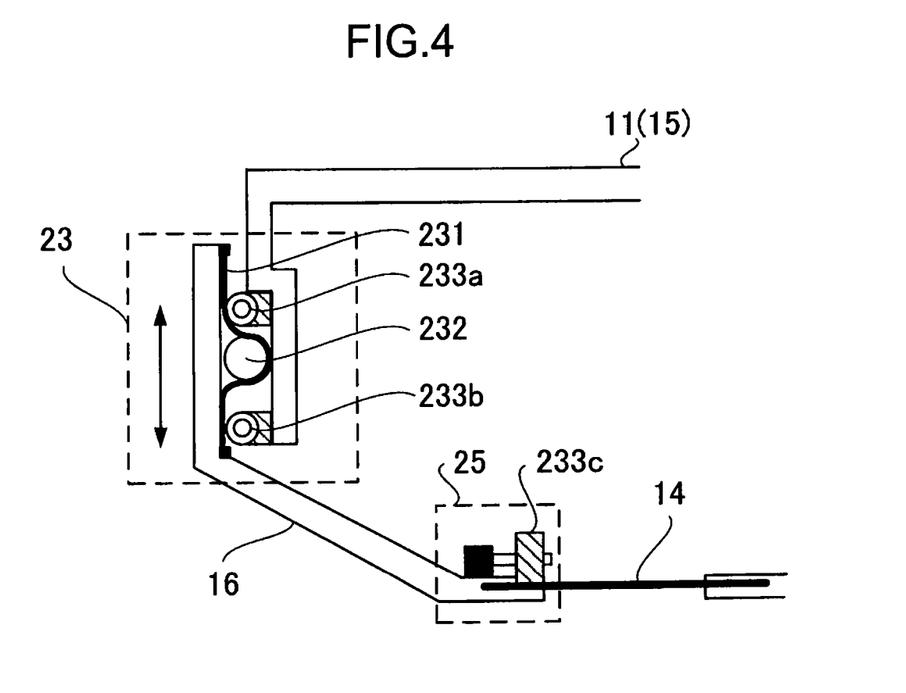
FIG. 4 shows one example of a slide mechanism unit and a tension adjustment unit according to the embodiment.

FIG. 2 is a cross-sectional diagram of a dome-diameter variable structure of the X-ray CT device taken along plane X-Z according to the present embodiment. FIG. 3 is a front view thereof. FIG. 4 shows one example of a slide mechanism unit and a tension adjustment unit in the dome-diameter variable structure.

As shown in FIG. 2, the dome-diameter variable structure of the present embodiment includes a dome-diameter driving unit 21, which drives in such a way that the dome diameter of the gantry dome 13 can be changed in response to a control instruction from a system control unit (81) described later; and a cover sheet adjustment unit 22, which adjusts a sheet length of the dome cover sheet 14 as the dome diameter changes.

The dome-diameter driving unit 21 controls slide mechanisms 23 on the sides of the front dome cover 11 and rear dome cover 12. The slide mechanisms 23 are placed between the fixed cover 15 and a plurality of segmented movable covers 16, and are used for the expansion and contraction of the dome diameter.

The cover sheet adjustment unit 22 includes a cover sheet expansion/contraction unit 24, which adjusts the length of the dome cover sheet 14 in such a way that the sheet length becomes most suitable for the changed dome diameter; and a tension adjustment unit 25, which creates tension on the dome cover sheet 14 in such a way that the movable covers 16 and the dome cover sheet 14 are in close contact with each other even when the dome diameter is changed.

As shown in FIG. 3, for example, the movable cover 16 is divided into four equal segments. The slide mechanisms 23, which are disposed between the movable covers 16 and the fixed cover 15, enable each movable cover 16 to move in a radial direction as indicated by arrow.

FIG. 4 shows one example of a slide mechanism 23. The slide mechanism 23 includes a rubber 231 and a motor 232, which are disposed on the side of the movable cover 16; and idlers 233a and 233b, which are fixed on the side of the fixed cover 15. As the motor 232 rotates, the movable cover 16 slides with respect to the fixed cover 15. The slide mechanism 23 may be a linear motor.

After each movable cover 16 moves in a radial direction, a gap emerges between the movable covers 16. The gap is absorbed by the elastic material 17 so that the inside of the gantry 10 becomes invisible.

For the cover sheet adjustment unit 22, suppose that the dome cover sheet 14 is in the shape of a strip. For example, in one example of the structure of the cover sheet expansion/contraction unit 24, the cover sheet expansion/contraction unit 24 is so structured that one side of the strip-shaped dome cover sheet 14 is fixed to the internal wall surface of the gantry dome 13, and the other side is pulled by a spring shown in FIG. 3 or the like. When the dome diameter becomes larger, the spring expands. When the dome diameter becomes smaller, the contractive force of the expanded spring is used in such a way that the dome cover sheet 14 is automatically pulled.

In order for the dome cover sheet 14 to track the dome diameter without being slack at a time when the dome diameter is changed, as shown in FIG. 4, the tension adjustment unit 25 is placed on the dome cover sheet 14. To the tension adjustment unit 25, for example, an idler 233c or the like is attached so that tension is constantly imposed on the dome cover sheet 14, which is therefore in close contact with the movable cover 16. As a result, the circular shape of the gantry dome 13 is maintained.

As described above, according to the first embodiment, a plurality of segmented movable covers move in radial directions. Therefore, it is possible to change the dome diameter.

Second Embodiment

Figure 5:
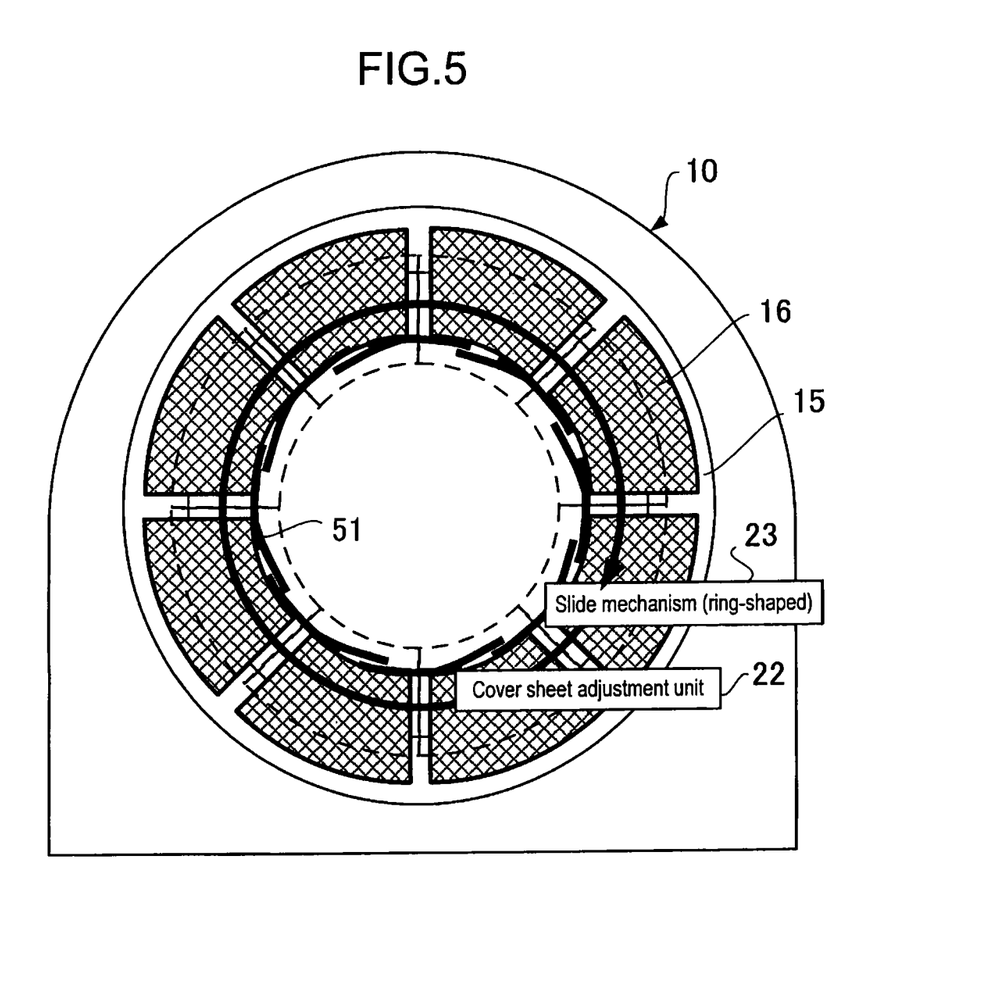
FIG. 5 is a front view of a dome-diameter variable structure of an X-ray CT device according to a second embodiment of the present invention.
Figure 6:
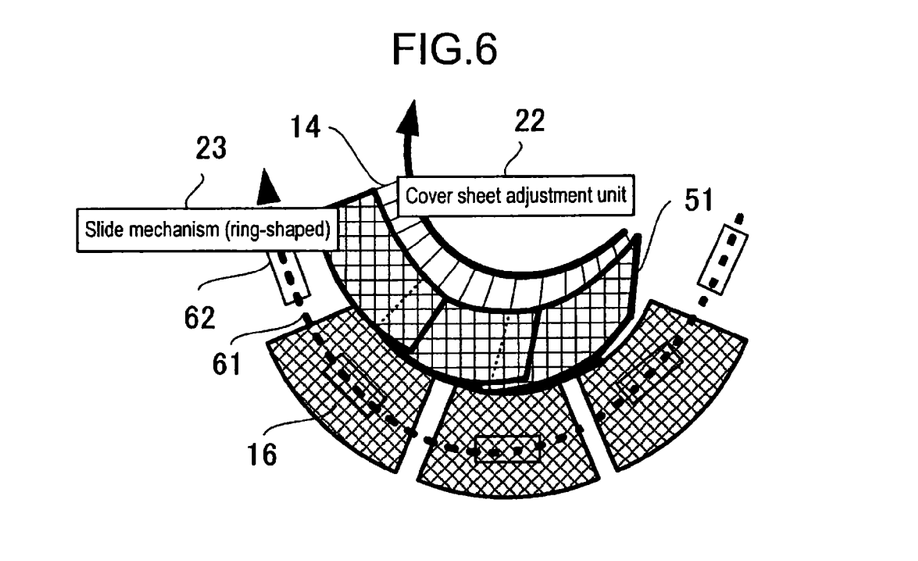
FIG. 6 is a detail view of the dome-diameter variable structure according to the embodiment.

According to the present embodiment, what is employed as the slide mechanism is a mechanism that slides in a ring-shaped direction. FIG. 5 is a front view of a dome-diameter variable structure of an X-ray CT device having a ring-shaped slide mechanism. FIG. 6 is a detail view of the dome-diameter variable structure.

In the dome-diameter variable structure of the present embodiment, eight equally divided movable covers 16 are provided, and a telescopic structural unit 51 is also provided for each of the movable covers 16. The eight movable covers 15 are assembled together to form a circular telescopic structure as a whole.

According to the circular telescopic structure described herein, adjoining telescopic structural units 51 of the movable covers 16 engage with each other, thereby enabling the dome diameter to expand or contract, with the dome-diameter shape, which is substantially in the shape of a circle, being maintained. Accordingly, in order to allow the dome diameter to change, an engaging portion of each telescopic structural unit 51 includes a structure capable of sliding.

As indicated by arrow in FIG. 5, the slide mechanism 23 (ring-shaped) sets the dome diameter using the length of a wire or the like in response to an instruction from the dome-diameter driving unit 21, thereby changing the dome diameter. That is, by pushing or pulling the wire running through the circular telescopic structure according to the same principles as those of a drawstring bag, the telescopic structure is expanded and contracted, thereby changing the dome diameter. Even though not shown in the diagram, a gap between the movable covers 16 is absorbed by elastic material as in the first embodiment, so that the inside of the rotation unit becomes invisible.

The cover sheet adjustment unit 22 may be the same in structure as that in the first embodiment. As an operation of changing the dome diameter goes on, the cover sheet adjustment unit 22 is so structured that one side of the strip-shaped dome cover sheet 14 is fixed, and the other side is pulled by a spring or the like.

As shown in FIG. 6, each movable cover 16 and a telescopic structural unit 51 are fixed and formed integrally. Furthermore, on a rear surface of each movable cover 16, for example, cylindrical wire guides 62 are disposed so as to guide a wire 61 indicated by dotted arrow. The wire guide 62 helps to maintain the circular shape of the dome.

As described above, according to the second embodiment, a plurality of segmented movable covers are assembled together with the circular telescopic, and are also so designed as to slide in a ring-shaped direction. Therefore, it is possible to change the dome diameter of the gantry dome.

Third Embodiment

Figure 7:
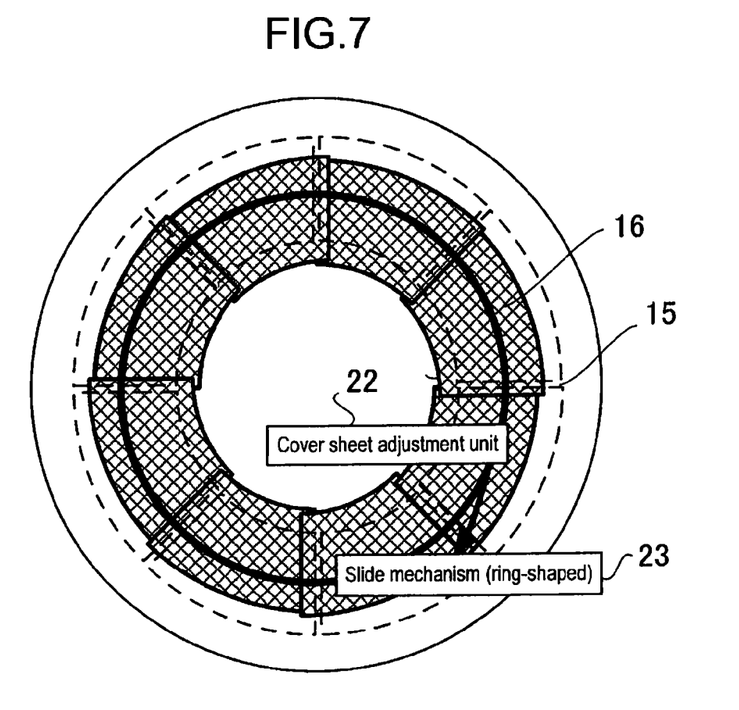
FIG. 7 is a front view of a dome-diameter variable structure of an X-ray CT device according to a third embodiment of the present invention.

What is shown in the second embodiment is a telescopic structure capable of a direction in which the dome diameter expands. According to the present embodiment, a circular telescopic structure capable of a direction in which the dome diameter contracts will be described.

Each movable cover 16 is so designed as to be a telescopic structural unit. In a direction in which the dome diameter contracts, each movable cover 16 overlaps in an adjacent movable cover 16, forming a circular telescopic structure.

When the present embodiment is designed in conjunction with the second embodiment, it becomes possible to expand and contract the dome diameter.

Fourth Embodiment

Figure 8:
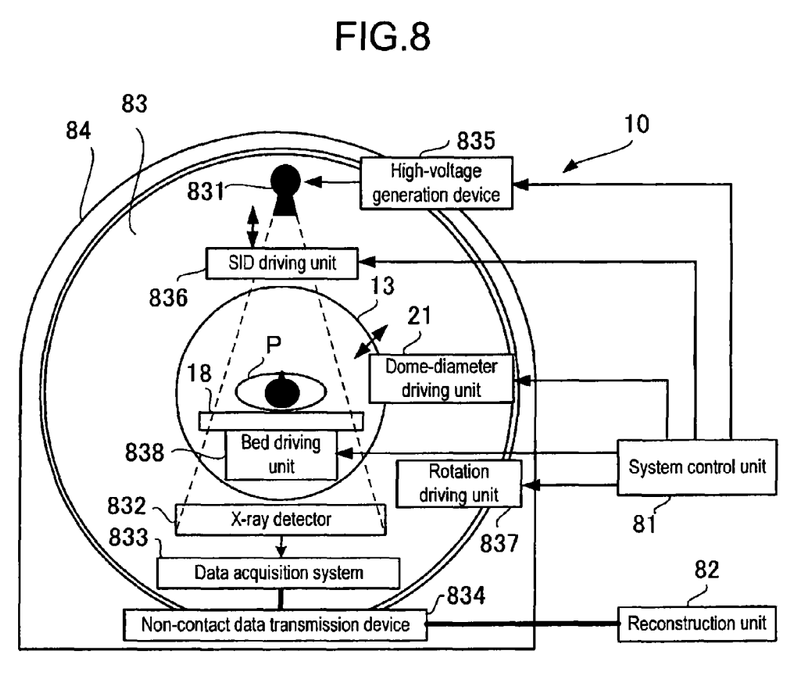
FIG. 8 is a block configuration diagram showing an X-ray CT device according to a fourth embodiment of the present invention.

According to the present embodiment, an X-ray CT device having the dome-diameter variable structure, which has been described in the first to third embodiments, will be explained. FIG. 8 shows an X-ray CT device having the dome-diameter variable structure. The X-ray CT device of the present embodiment includes a gantry 10, which is used to scan a test subject P with X rays; a bed 18, which transfers the test subject P into a gantry dome 13; a system control unit 81, which controls the entire X-ray CT device; and a reconstruction unit 82, which is a computer that processes projection data obtained from the gantry 10 to reconstruct a medical image.

The internal part of the X-ray CT device gantry 10 having the dome-diameter variable structure includes a rotation unit 83, which rotates around the test subject P; and a fixed unit 84, which consists of the other parts. The rotation unit 83 includes an X-ray tube 831 that generates X rays; an X-ray detector 832 that detects X rays passing through the test subject P after being emitted from the X-ray tube 831; a data acquisition system (DAS) 833 that converts detection data of the X-ray detector 832 into digital data and collects the data; and a non-contact data transmission device 834 that transmits projection data, which are acquired by the data acquisition system 833, out of the rotation unit 83 to the reconstruction unit 82 in a non-contact manner.

The system control unit 81 includes a high voltage generation device 835 that generates a voltage, which is applied to the X-ray tube 831 to generate X rays; a dome diameter driving unit 21 that changes the dome diameter of the gantry dome 13; an SID driving unit 836 that changes the distance (SID) between the X-ray tube 821 and the X-ray detector 832 as the dome diameter changes; a rotation driving unit 837 that rotates the rotation unit 83 on the basis of a scanning condition such as helical scanning; and a bed driving unit 838 that moves the bed 18, on which the test subject P lies, into the gantry dome 13.

The reconstruction unit 82 reconstructs a medical image, which is required for diagnosis, from the projection data transferred from the non-contact data transmission device 834. The reconstructed medical image is displayed on a monitor or the like, which is connected to the reconstruction unit 82 and not shown in the diagram. Moreover, as the dome diameter is changed by the dome-diameter driving unit 21 and as the SID is changed by the SID driving unit 836, medical images of varying image-taking magnifications can be reconstructed and displayed on a monitor or the like. The system control unit 81 and the reconstruction unit 82 are generally formed based on high-performance computers.

Figure 9:
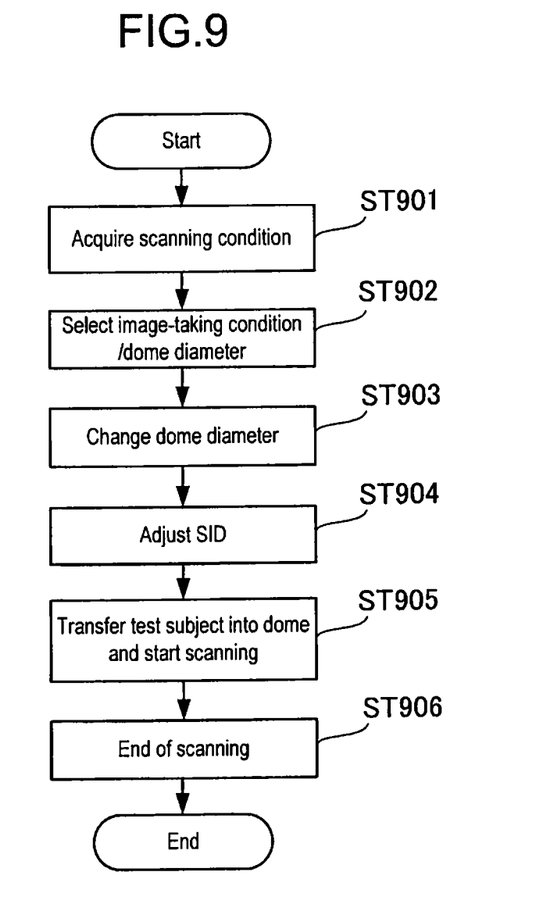
FIG. 9 is a flowchart showing a scanning procedure of the X-ray CT device according to the embodiment.

The following describes a scanning procedure for normal and magnification radiography with reference to FIG. 9.

First, a doctor or laboratory technician makes the test subject P lie on the bed 18, and inputs a scanning condition for a medical image of a to-be-acquired part of the test subject P. At step ST901, the system control unit 81 obtains the scanning condition input.

At step ST902, the doctor or laboratory technician selects an image-taking mode type, such as normal or magnification radiography, or an image-taking magnification. If there is a need to increase the dome diameter because of the physique of the test subject P even when the image-taking magnification remains unchanged, the size of the dome diameter is selected.

At step ST903, the system control unit 81 calculates the most appropriate dome diameter on the basis of an input condition, such as the image-taking mode, image-taking magnification, physique of the test subject P or the like, which is selected at step ST902. The system control unit 81 controls the dome-diameter driving unit 21 in such a way that the dome has the calculated dome diameter. At step ST904, when the image-taking mode type, such as magnification radiography, or the image-taking magnification is changed, the system control unit 81 adjusts the SID so as to have the most appropriate magnification.

At step ST905, the bed driving unit 838 is controlled so that the test subject P lying on the bed 18 moves into the gantry dome 13 before scanning starts.

At step ST906, the scanning that meets the image-taking mode/image-taking condition comes to an end. The resulting projection data is reconstructed by the reconstruction unit 82 as a medical image.

As described above, according to the fourth embodiment, the dome diameter of the gantry dome 13 and the SID are variable, enabling medical images of varying image-taking magnifications to be obtained.

Other Embodiments

According to the first to third embodiments, the cover sheet adjustment unit 22 is provided. The dome cover sheet 14, which functions as an irradiation window through which X rays emitted from the X-ray tube 831 pass, is provided in terms of safety with the aim of preventing a test subject or operator from putting a hand or the like into the high-speed rotation unit by accident. At present, the dome cover sheet 14 is made of a transparent or semi-transparent sheet. Specifically, Mylar, a PET (polyethylene terephthalate) material having poor elasticity, is used in many cases.

However, the dome cover sheet 14 can be made of a material that allows X-rays to pass therethrough without being attenuated and can be so formed that the test subject cannot put a hand or the like therein. Therefore, Mylar may not be used. That is, if the dome cover sheet 14 is made up of a cylindrical elastic material having less X-ray attenuation, the shape can be flexibly changed with respect to the changing dome diameter. In such a case, the functions of the cover sheet adjustment unit 22 can be automatically achieved.

Therefore, according to the fourth embodiment, since the dome cover sheet is made up of a cylindrical elastic material having less X-ray attenuation, the advantage is that the dome cover sheet is also automatically changed as the dome diameter varies.

As described above, according to the X-ray CT device of the present embodiment, the dome diameter can be made smaller because the exterior cover includes a mechanism for changing the dome diameter. The dome diameter can be made smaller, and therefore an internal space can be reserved. As a result, magnification radiography, which is a process of taking an image by bringing the X-ray tube closer to the X-ray detectors, is possible. Moreover, at the time of normal radiography, the dome diameter can be made larger. Therefore, it is possible to handle a person of large physique in a flexible manner, and to meet other users' needs.

The present invention is not limited to the above embodiments, and can be altered in various ways. For example, the shape of movable covers shown in the above embodiments is given for illustrative purposes only. The number of segments or the like may vary when necessary. The larger the number of segments, the more circular the dome shape becomes.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT device, comprising:
a front dome cover and rear dome cover that include a fixed cover and a plurality of segmented movable covers;
a slide mechanism that enables the movable covers to slide relative to the fixed cover; and
a dome-diameter driving unit that controls the slide mechanism to change a dome diameter of a gantry dome.

2. The device according to claim 1, wherein
the slide mechanism makes each of the movable covers slide radially relative to the center of the gantry dome.

3. The device according to claim 2, further comprising:
a dome cover sheet that is on an internal wall surface of the gantry dome made up of the front dome cover and rear dome cover and serves as an X-ray irradiation window; and
a cover sheet adjustment unit that adjusts a cover sheet length of the dome cover sheet.

4. The device according to claim 3, wherein
the cover sheet adjustment unit adjusts the cover sheet length in away that tracks the changing of the dome diameter of the gantry dome.

5. The device according to claim 4, wherein
an elastic material is provided between the adjoining movable covers.

6. The device according to claim 1, wherein
the slide mechanism makes each of the movable covers slide in a ring-shaped manner relative to the center of the gantry dome.

7. The device according to claim 6, wherein
each of the movable covers includes a telescopic structural unit, and the gantry dome of a circular telescopic structure is formed by each movable cover.

8. The device according to claim 7, further comprising:
a dome cover sheet that is on an internal wall surface of the gantry dome made up of the front dome cover and rear dome cover and serves as an X-ray irradiation window; and
a cover sheet adjustment unit that adjusts a cover sheet length of the dome cover sheet.

9. The device according to claim 8, wherein
the cover sheet adjustment unit adjusts the cover sheet length in away that tracks the changing of the dome diameter of the gantry dome.

10. The device according to claim 9, wherein
an elastic material is provided between the adjoining movable covers.

11. An X-ray CT device, comprising:
an X-ray tube;
an X-ray detection unit that detects X rays emitted from the X-ray tube;
a reconstruction unit that converts output signals of the X-ray detection unit into digital signals to collect and reconstructs a medical image;
a front dome cover and rear dome cover that include a fixed cover and a plurality of segmented movable covers;
a slide mechanism that enables the movable covers to slide relative to the fixed cover;
a dome-diameter driving unit that controls the slide mechanism to change a dome diameter of a gantry dome; and
a SID driving unit that changes a distance between the X-ray tube and the X-ray detection unit.

12. The device according to claim 11, wherein
the slide mechanism makes each of the movable covers slide in a radial or ring-shaped direction relative to the center of the gantry dome.

13. The device according to claim 12, further comprising:
a dome cover sheet that is on an internal wall surface of the gantry dome made up of the front dome cover and rear dome cover and serves as an X-ray irradiation window; and
a cover sheet adjustment unit that adjusts a cover sheet length of the dome cover sheet.

14. The device according to claim 13, wherein
the cover sheet adjustment unit adjusts the cover sheet length in a way that tracks the changing of the dome diameter of the gantry dome.

15. The device according to claim 14, wherein
an elastic material is provided between the adjoining movable covers.

16. The device according to claim 15, wherein
the dome-diameter driving unit and the SID driving unit are controlled in such a way that the dome diameter and SID are set so as to meet an image-taking magnification condition.

* * * * *